US006966236B2

(12) United States Patent
Charters et al.

(10) Patent No.: US 6,966,236 B2
(45) Date of Patent: Nov. 22, 2005

(54) SELECTIVE PROFILING OF BULK BUILDING MATERIAL FOR CHARACTERIZATION USING A CONCRETE CONTAMINATION PROFILING TECHNOLOGY

(75) Inventors: Grant Jones Charters, Arlington, TX (US); Sudesh Aggarwal, Arlington, TX (US)

(73) Assignee: New Millennium Nuclear Technologies, LLP, Arlington, TX (US)

( * ) Notice: Subject to any disclaimer, the term of this patent is extended or adjusted under 35 U.S.C. 154(b) by 151 days.

(21) Appl. No.: 10/412,066

(22) Filed: Apr. 10, 2003

(65) Prior Publication Data

US 2003/0213315 A1 Nov. 20, 2003

Related U.S. Application Data

(60) Provisional application No. 60/371,971, filed on Apr. 12, 2002.

(51) Int. Cl.[7] .......................... G01N 1/08; G01N 33/38; G01N 23/00; G01T 7/02; G01T 7/00
(52) U.S. Cl. ..................... 73/866; 73/864.43; 73/864.34
(58) Field of Search .................... 73/864.33–864.34, 73/866, 864.43, 863.23, 28.01, 28.04, 31.03; 436/174, 177; 250/304, 395, 391–392, 358.1, 390.04, 390.02

(56) References Cited

U.S. PATENT DOCUMENTS

| | | | | | |
|---|---|---|---|---|---|
| 4,437,333 A | * | 3/1984 | Hands | ...................... | 73/866 X |
| 4,483,205 A | * | 11/1984 | Bellaiche et al. | ........ | 73/863.23 |
| 4,616,515 A | * | 10/1986 | Dancoine | ............. | 73/863.23 X |
| 4,754,655 A | * | 7/1988 | Parker et al. | ........ | 73/863.23 X |
| 4,936,153 A | * | 6/1990 | Klit | ...................... | 73/864.33 X |
| 5,939,330 A | * | 8/1999 | Peterson | ...................... | 436/180 |
| 6,158,509 A | * | 12/2000 | Peterson | ...................... | 166/264 |
| 6,289,714 B1 | * | 9/2001 | Tartre | .................. | 73/864.43 X |
| 6,446,514 B1 | * | 9/2002 | Danylewych-May et al. | ................... | 73/863.23 X |
| 6,466,637 B2 | * | 10/2002 | Bowen et al. | ....... | 73/863.23 X |

FOREIGN PATENT DOCUMENTS

| | | | | | |
|---|---|---|---|---|---|
| EP | 315277 A1 | * | 5/1989 | ........... | B23B/51/04 |
| JP | 62222141 A | * | 9/1987 | ............ | G01N/1/04 |
| JP | 2002055031 A | * | 2/2002 | ............ | G01N/1/08 |

* cited by examiner

Primary Examiner—Thomas P. Noland
(74) Attorney, Agent, or Firm—Haynes and Boone, LLP (57) ABSTRACT

Disclosed is a method and system to characterize the contamination levels of bulk materials, the method comprises drilling into the material, sampling material from the drill point at predetermined intervals, and analyzing the sampled material. Such an embodiment may be accomplished by using a drill with a specialized cutting and sampling head, drill bits, a sample collection units and a vacuum pump. The embodiment in conjunction with portable radiometric instruments produces a profile of radiological or chemical contamination through the material being studied.

15 Claims, 7 Drawing Sheets

SELECTIVE PROFILING OF BULK BUILDING MATERIAL FOR CHARACTERIZATION USING A CONCRETE CONTAMINATION PROFILING TECHNOLOGY

CROSS REFERENCE TO A RELATED APPLICATION

This application claims the benefit of the filing date of U.S. provisional patent application Ser. No. 60/371,971 filed on Apr. 12, 2002, the disclosure of which is incorporated herein by reference.

TECHNICAL FIELD

The invention relates in general to waste characterization, and in particular to a method and system for characterizing bulk building material.

BACKGROUND

The Department of Energy (DOE) is in the process of decontamination and decommissioning (D&D) many of its nuclear facilities throughout the United States. These facilities are typically chemically or radiologically contaminated. For instance, within the next few decades, millions of cubic meters of bulk building material, such as concrete, brick, and mortar, will be removed from nuclear facilities across the United States as a result of these decontamination and decommissioning activities. Material that has been exposed to radiological or chemical contamination must undergo an expensive treatment or disposal process. Not all of the decommissioned material is contaminated. Thus, segregating the contaminated material from the "clean" material can significantly reduce D&D costs and expenses. In order to segregate the contaminated material from the clean material, some form of analysis or "characterization" is performed to determine the extent and amount of contamination at any given facility.

If the radiological history indicates that a particular facility or structure may have been exposed to radiation or chemical contaminants, an analysis should be conducted to determine if the building materials contain residual radioactive or chemical material. For instance, if the concrete has been determined, through the radiological history, as not being radioactive and not containing residual radioactive material, then the concrete can be released or removed. However, if the radiological history will not support determination that the concrete does not contain residual radioactive material, then the property should be treated as either (1) known to be contaminated or previously contaminated or (2) possibly contaminated. In either case, a determination should be performed to determine the extent of the contamination. Concrete known to be either contaminated, previously contaminated, or possibly contaminated must be comprehensively surveyed before release to demonstrate compliance with release limits.

Since radiochemicals or chemicals on or in contaminated concrete are typically encapsulated in the complex building matrix, cost effective removal and disposal of the contaminated material fraction require techniques to penetrate the concrete to assess the levels of contamination within the matrix prior to the release of the material. If the concrete material is volumetrically contaminated, surface removal techniques may not provide adequate decontamination.

Currently, in order to determine volumetric contamination, cores are drilled from material, such as concrete. The concrete cores are shipped to certified laboratories where the concrete is run through a battery of tests to determine the extent of contaminants. However, in addition to delays, concrete boring often results in cross-contamination, which can lead to inaccurate results and increase the amount of waste generated. Additionally, some contaminants volatilizes out of the concrete. This volatilization can lead to air borne problems in the immediate vicinity of the core and additional cross contamination.

What is needed, therefore, is a method and apparatus which can quickly and accurately volumetrically characterize building materials, such as concrete, while minimizing cross-contamination and waste.

SUMMARY

In response to these and other problems, in one embodiment, a method and system is disclosed to volumetrically characterize the waste content of materials. In one embodiment, the method comprises drilling into the material, sampling material from the drill point at predetermined intervals, and analyzing the sampled material. Such an embodiment may be accomplished by using a drill with a specialized cutting and sampling head, drill bits, a sample collection unit and a vacuum pump. The embodiment in conjunction with portable chemical and radiometric instruments produces a profile of radiological or chemical contamination through the material being studied.

DETAILED DESCRIPTION

The invention is generally directed to a method for contamination profiling and characterization of bulk building materials containing or possibly containing radiochemical or chemical contamination. It is understood, however, that the following disclosure provides many different embodiments, or examples, for implementing different features of the invention. Well known elements are presented without detailed description in order not to obscure the present invention in unnecessary detail. For the most part, details unnecessary to obtain a complete understanding of the present invention have been omitted inasmuch as such details are within the skills of persons of ordinary skill in the relevant art.

Figure 1:
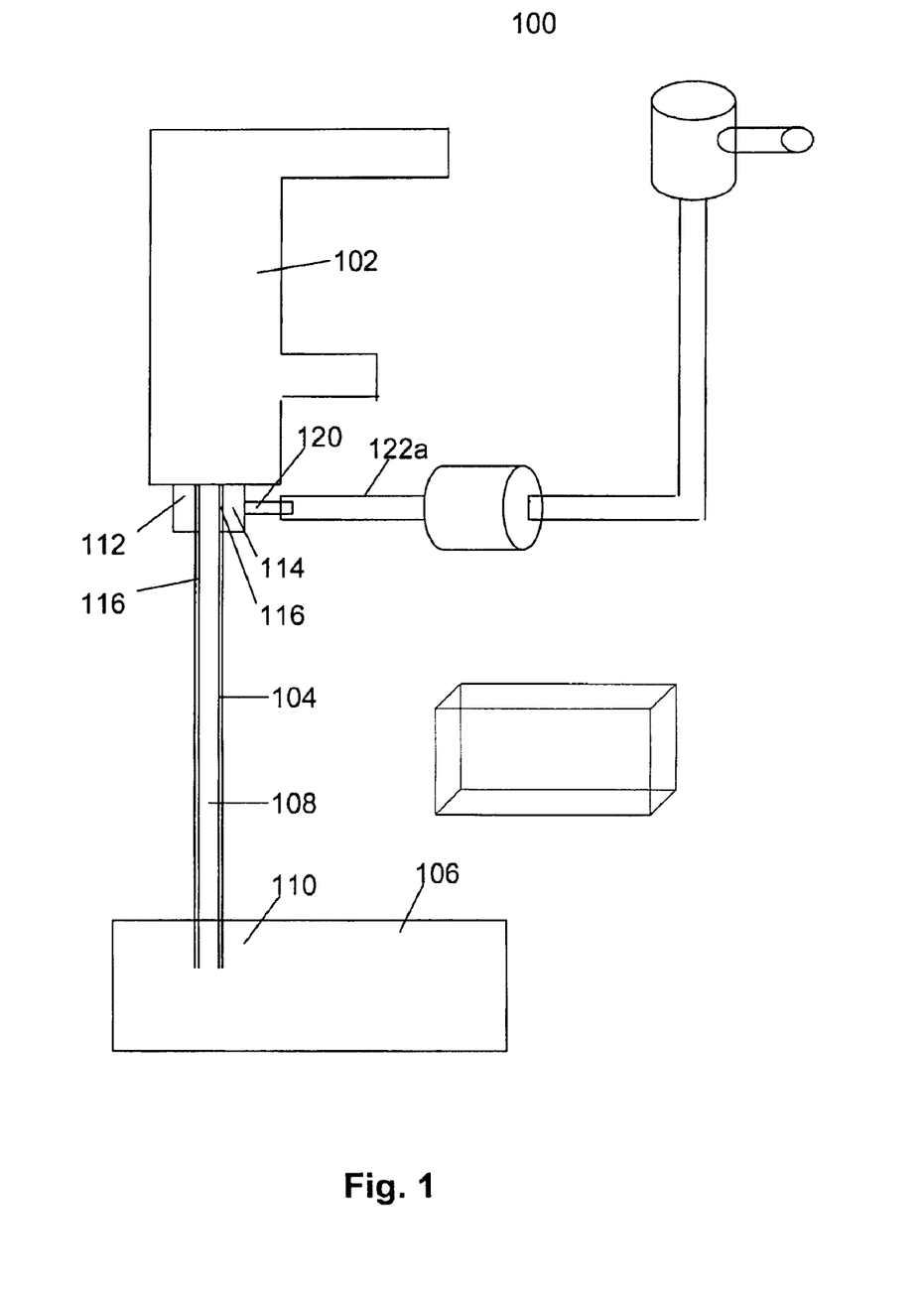
FIG. 1 is a schematic illustration of a system which may be used to employ various embodiments of the present invention.

Turning to FIG. 1, there is illustrated a system 100 for employing some of the embodiments of the present invention. A drill 102 is coupled to a drill bit 104 in a known manner. The drill 102 may be any type of drill capable of drilling into a portion of bulk material 106, which may be concrete, brick, grout, steel or any other building material which may have been exposed to contamination. The drill 102 may operate in a hammer action mode to penetrate the surfaces of the bulk material 106.

The drill bit 104 may be a tubular or hollow core bit defining an air flow passage 108. The drill bit 104 may be made of a material such as tungsten carbide and have a drilling end 110 and a connecting end 112. In some embodiments, the exterior of the drill bit 104 may be marked in longitudinal increments (not shown) so that an operator can visually determine the depth of the penetration into the bulk material 106. At least one opening 114 is positioned close to the connecting end 112 and through the wall of the drill bit 104.

A manifold 116 surrounds the connection end 112 and the opening 114. The manifold 114 may be coupled to the drill 102 such that it does not rotate. The drill bit 104 passes through an opening 118 in the manifold which allows the drill bit to rotate and move longitudinally with respect to the manifold 114. A port 120 may be located in the side of the manifold 116 which may connect to a vacuum line 122a. In the illustrative embodiment, the vacuum line 122a is coupled to a filter unit 124. The filter 124 may be an in-line filter or a series of in-line filters and water traps. For example, in one embodiment, the filter unit comprises of three, 350 cm³, 4 um filter units. A vacuum line 122b may be coupled to the filter unit 124 to act as an exhaust line. The vacuum line 122b may also be coupled to a vacuum source 126, such as a vacuum pump. The vacuum source may have an exhaust port 127 which may have additional filtration (not shown).

Additionally, the system may use a analysis equipment 128 to analyze samples removed from the filter unit 124. Such equipment may be in-situ and portable. In one embodiment, the analysis equipment is a portable liquid scintillation counter and gamma counting system. Such a system may allow for the detection of tritium contamination at depth within the building material matrix in real time.

Figure 2:
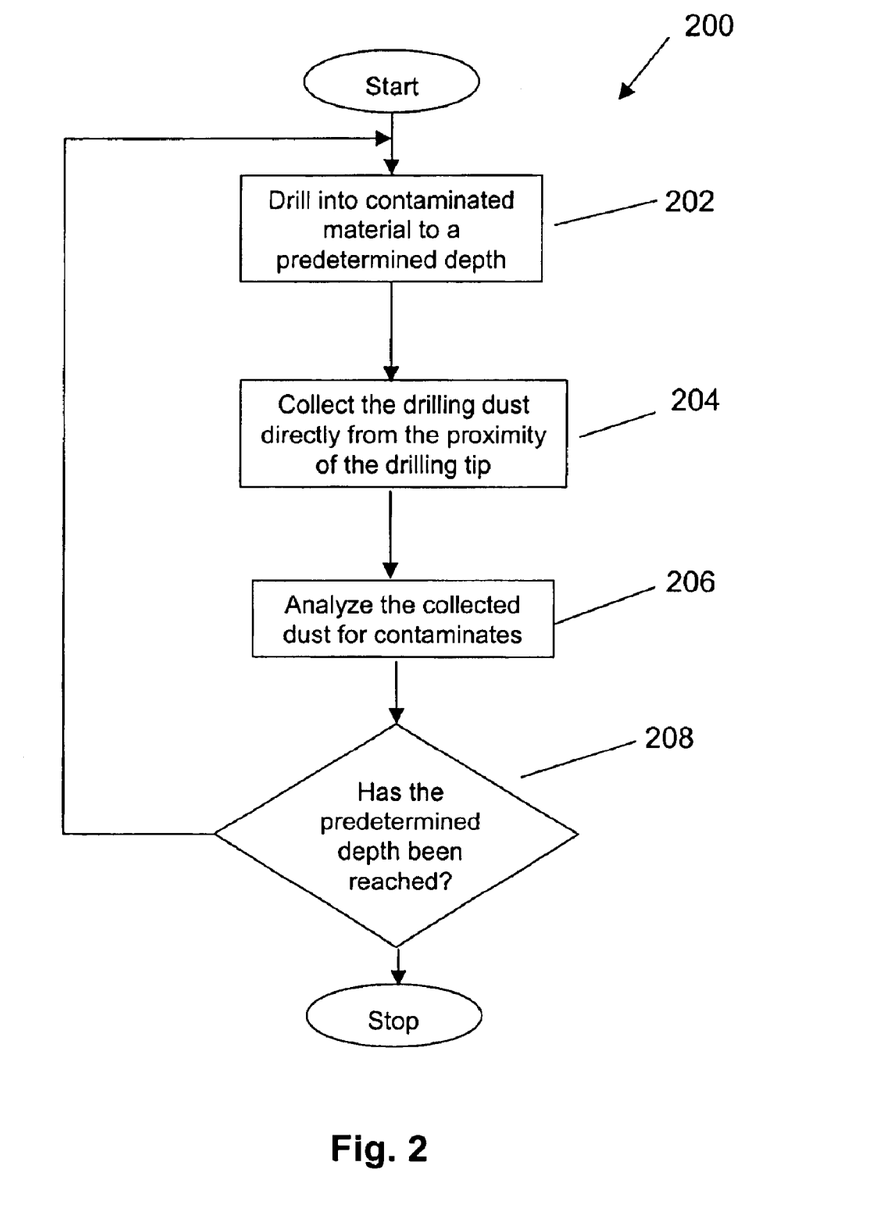
FIG. 2 is a flow diagram illustrating one embodiment of the present invention.

Turning now to FIG. 2, there is a process illustrating a method of using the system of FIG. 1. In step 202, an operator uses the drill 102 to drill into the contaminated bulk material 106 to a predetermined depth. For instance, samples of concrete could be profiled at predetermined depth increments (e.g., ⅛" or 1"). As the drilling end 110 of the drill bit 104 drills down to the required depth, drilling and/or hammering action of the drill causes the bulk material below the drill bit to be pulverized into dust. The vacuum source 126 causes a suction in the lines 122a and 122b, which are in hermetic communication with the air flow passage 108 of the drill bit 104. Due to vacuum within the air flow passage 108, the concrete dust flows up the air flow passage 108 and exits the opening 114 of the drill bit 104. The manifold 116 contains the dust and the vacuum force developed by the vacuum source 126 draws the dust through the port 120 and the vacuum line 122a where it can be collected on the filter unit 122. Thus, the dust can be quickly extracted away from the drilling end 110 of the drill bit 104 without fear of cross-contamination from the layers of concrete above the sample area (as would be the case with conventional drilling or boring equipment). If the filter unit 124 comprises a plurality of filters mounted in series, the sampled dust travels to the first inline filter where it is collected and prevented from traveling to a secondary filter unit, which acts as a secondary barrier for the vacuum source 126. Air passing through the primary and secondary inline filters may then pass through a volatile extraction unit to trap all volatiles released during sampling. Furthermore, the exhaust of the vacuum source 126 pump may have a filter built into the pump mechanism to prevent any extraneous dusts being released to the working environment.

In step 204, the dust may be collected for analysis by removing the first filter unit. In some embodiments, the filters may be screwed into a housing and sealed tight with a rubber o-ring to maintain containment of the dusts and the integrity of the high vacuum. The removal of the filter unit and its replacement may be achieved by a simple screwing of the filter housing onto the manifold of the housing. The collected dust may then be dispensed into a sealed containment vessel before being weighed out for appropriate radiometric measurement.

In step 206, the dust may be analyzed. A known mass of each incremental depth of dust sample may then be weighed out on a calibrated balance. The dusts may be presented in the best sample geometry for analysis by the appropriate portable instrumentation. The dusts constituted a mass of very fine particulate so minimizing self-absorption of any activity present.

The sample process may thus continue until a predetermined depth has been reached. The predetermined depth may be a physical measurement, (e.g., 6 inches) or whatever depth contains a predetermined level of contamination (e.g., whatever depth is below the background level for the contaminant in question). In other words, once the contamination levels drop below a predetermine contamination level, the sampling process at that location may stop.

Sampling may then begin at another location and the process repeated at various depths of interest. Thus profiling of data quality, quantity, and representativeness may be used to produce an activity profile from the hot spot surface into the bulk building material. The activity data obtained during the profiling process may be graphically quantified and transferred to building drawings as part of a detailed report of the radiological problem. This activity profile may then be expanded to ultimately characterize the facility and expedite waste segregation and facility closure at a reduced cost and risk.

In one actual test, the above system and method was in conjunction with a liquid scintillation counter system to detect tritium at depth within the building material matrix in real time. One embodiment was set up to take samples of concrete from a concrete slab to be profiled at ⅛-in increments at many points on the surface for the first 6 sample. This increased the mass of sample acquired, 0.1 g to 0.25 g is all that was needed for the portable Liquid Scintillation Counting equipment, the rest of the concrete dust is produced for the onsite laboratory to compare the contamination profile results and analyze for more diverse and complex contamination possibly present in the material sampled.

Figure 3A:
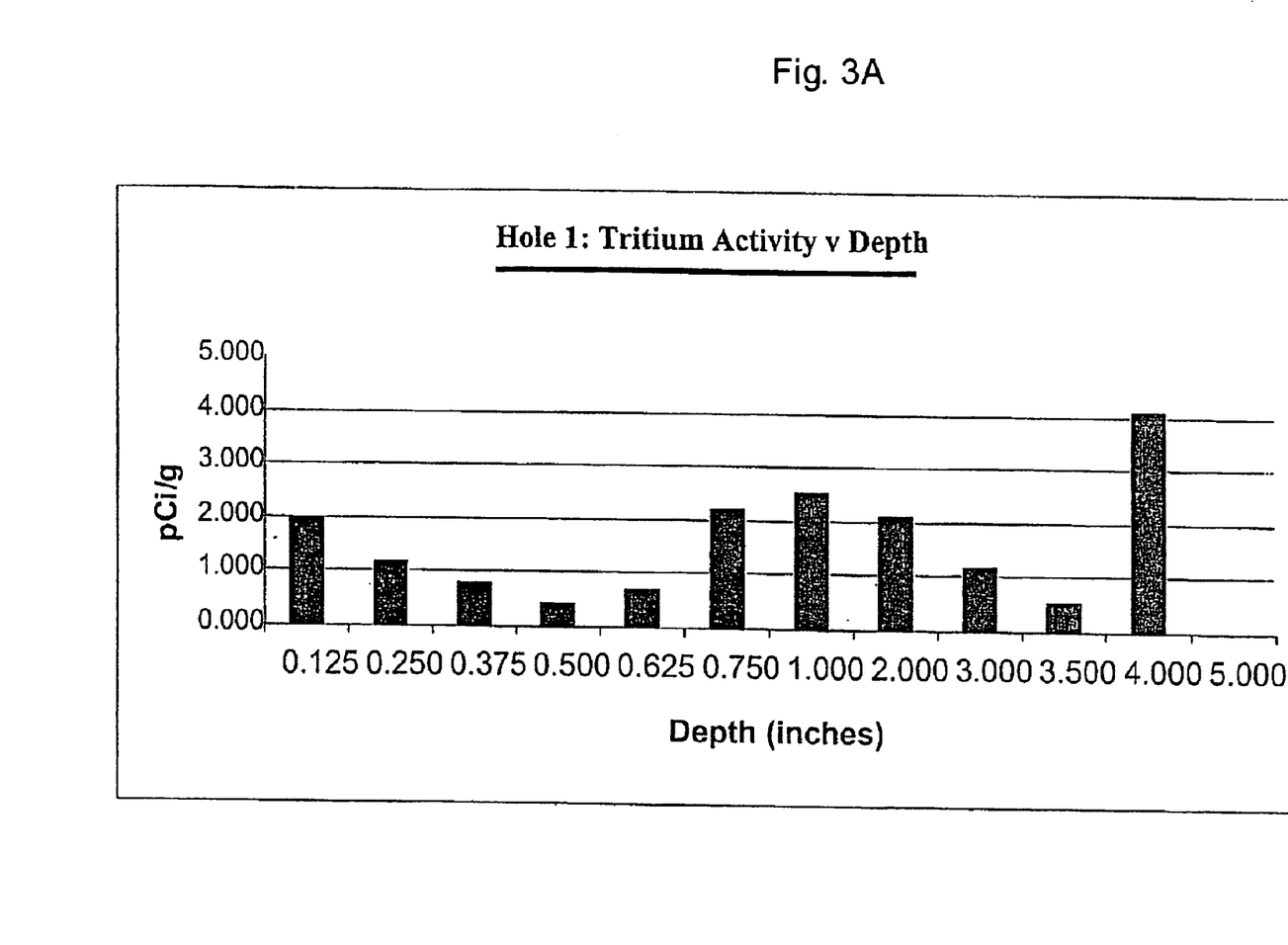
FIG. 3A is a graphic representation of the levels of tritium activity of an example contaminated concrete waste material.
Figure 3B:
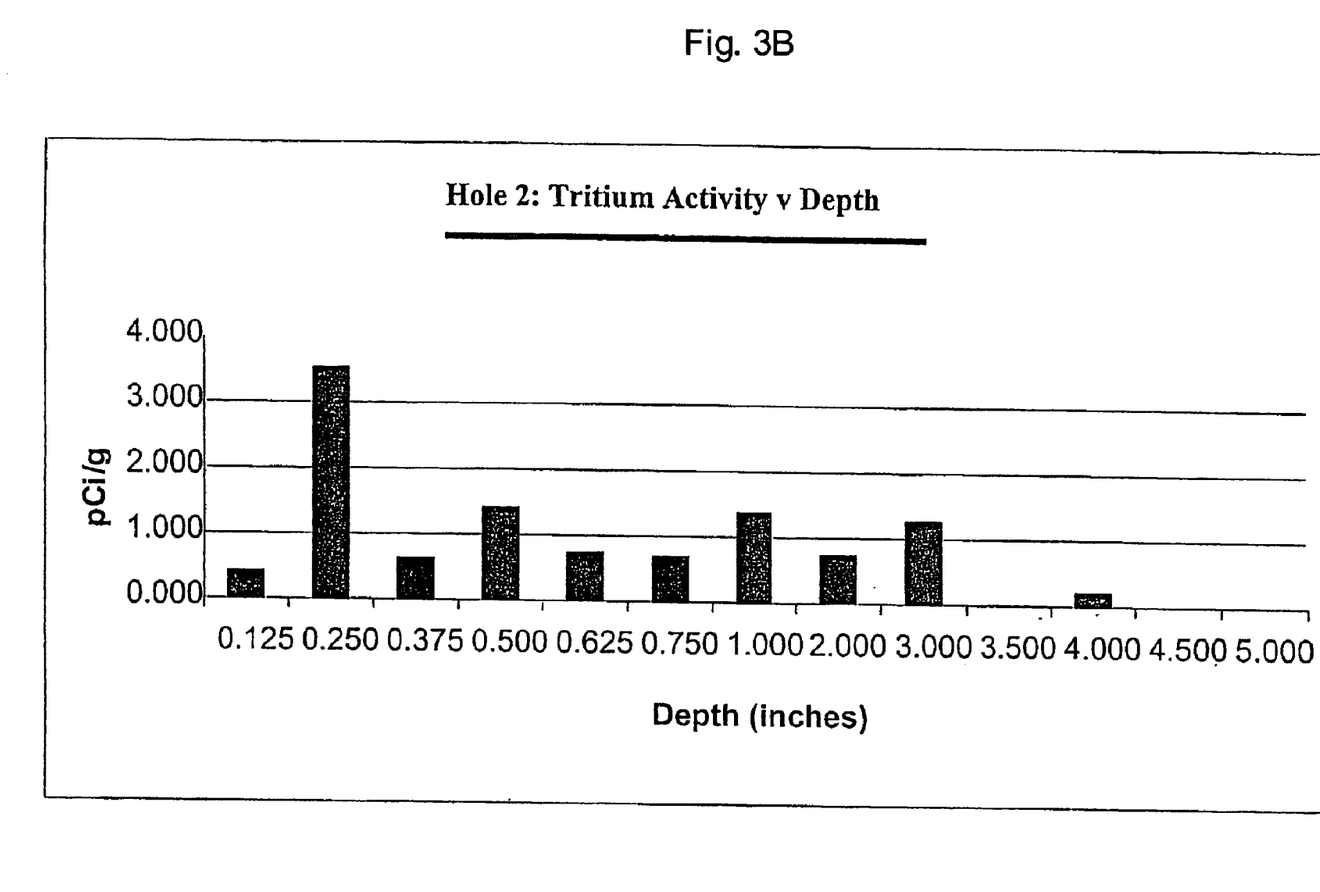
FIG. 3B is a graphic representation of the levels of tritium activity of an example contaminated concrete waste material at another position.
Figure 3C:
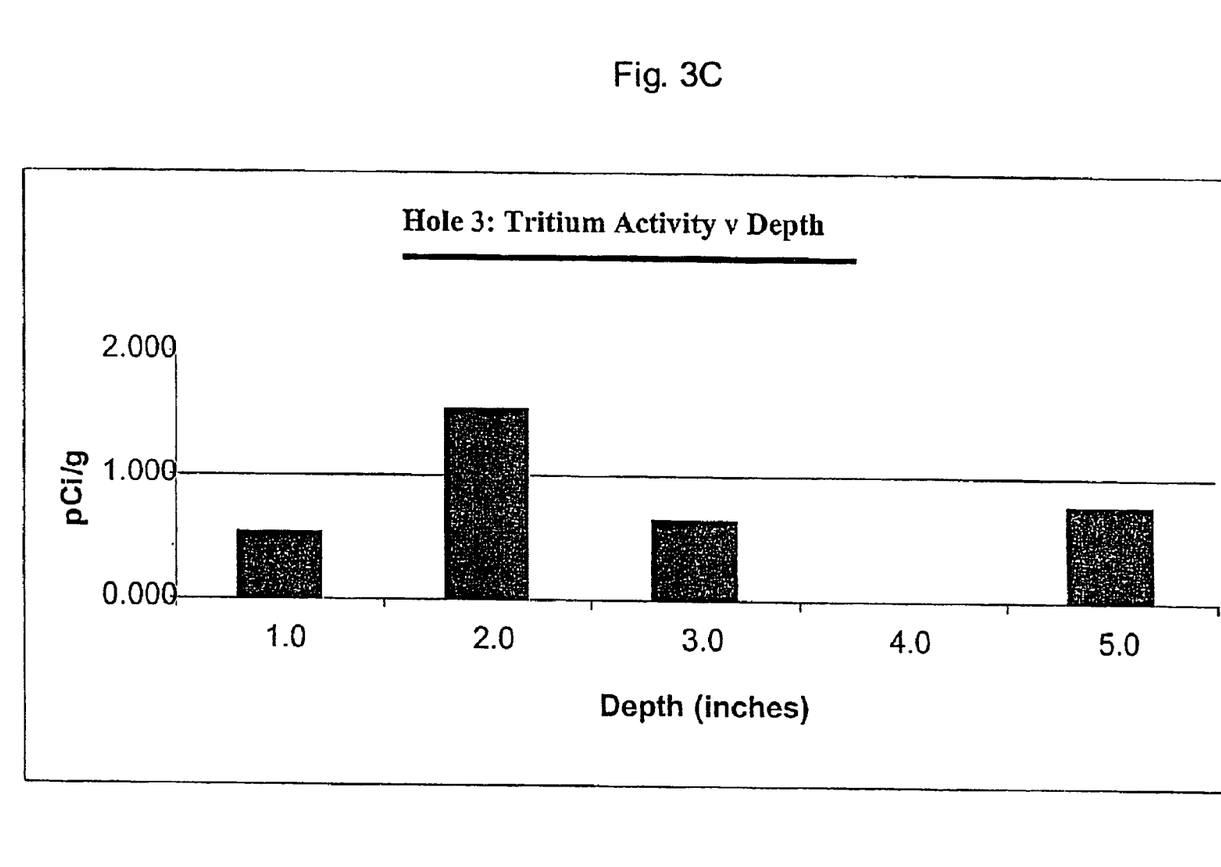
FIG. 3C is a graphic representation of the levels of tritium activity of an example contaminated concrete waste material at a third position at 1 inch incremental sampling positions.

The first inch at one sixteenth of an inch of sampling took approximately 40 minutes, and the samples acquired at inch increments took approximately 10 seconds. A known mass of each incremental depth of dust sample was weighed out on a calibrated balance. From the start of sampling to the completion of analysis, a total time of 20 minutes per sample was observed, which is a vast improvement in time and cost over the previous methods and a more representative sample is acquired in a safer and more precise manner. The combined results of the sampling and analysis process for the Tritium contaminated facility are set forth in TABLE 1 below and in bar chart FIGS. 3A, 3B, and 3C.

TABLE 1

Tritium Activity With Depth of the Concrete Slab of Mound Plan Tritium Room

| Depth (Inches) | Hole 1 (nCi/g) | Hole 2 (nCi/g) | Hole 3 (nCi/g) |
|---|---|---|---|
| 0.125 | 0.201 | 0.044 | NA |
| 0.25 | 0.116 | 0.352 | NA |
| 0.375 | 0.081 | 0.061 | NA |
| 0.5 | 0.044 | 0.144 | NA |
| 0.625 | 0.068 | 0.072 | NA |
| 0.75 | 0.221 | 0.068 | NA |
| 1 | 0.251 | 0.136 | 0.053 |
| 2 | 0.207 | 0.076 | 0.155 |
| 3 | 0.119 | 0.127 | 0.064 |
| 3.5 | 0.053 | <0.013 | NA |
| 4 | 0.409 | 0.023 | <0.013 |
| 4.5 | NA | <0.013 | NA |
| 5 | <0.013 | <0.013 | 0.077 |

Alternative Embodiments

Figure 4:
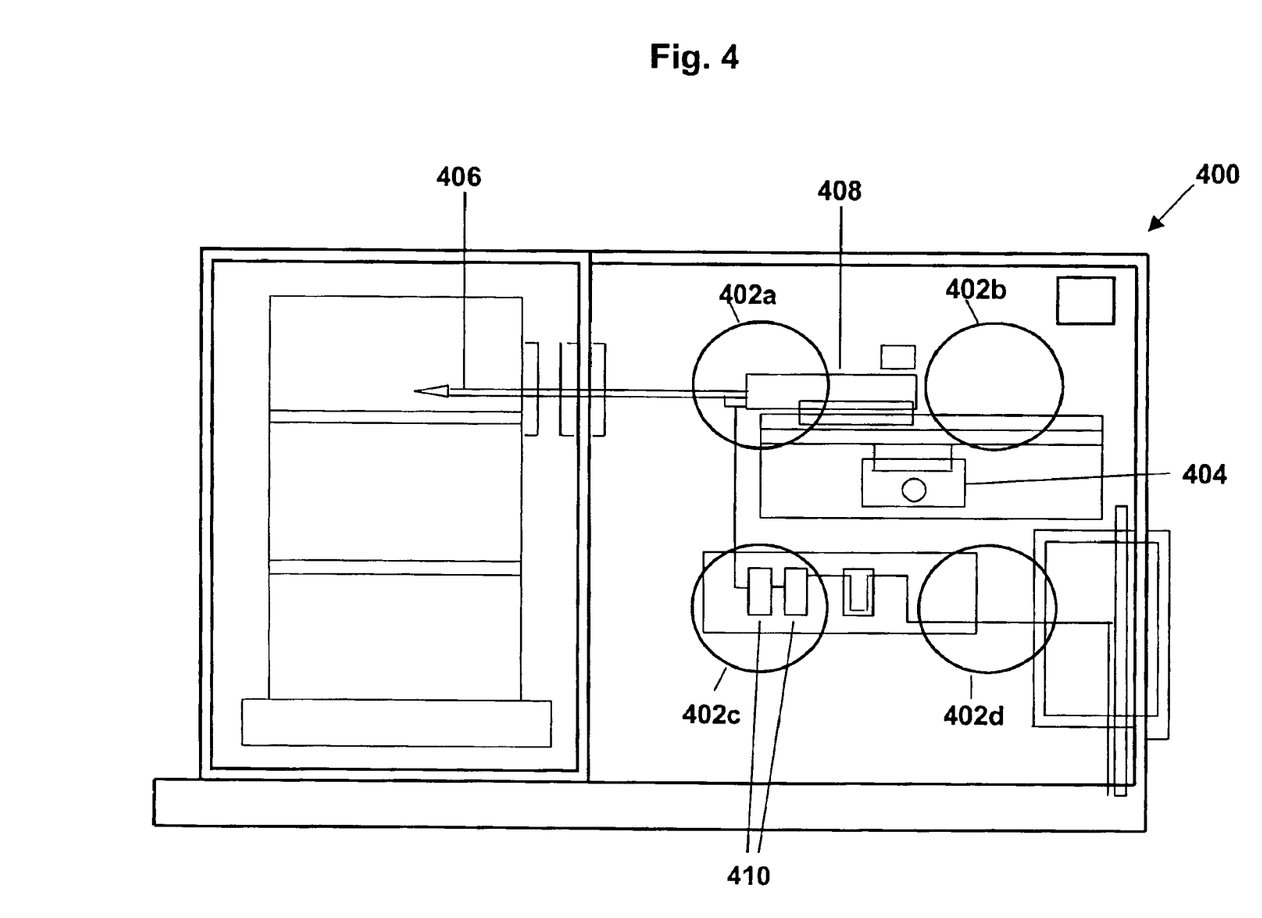
FIG. 4 is a schematic illustration of an alternative system.

An alternative embodiment is illustrated in FIG. 4, which is a transverse section view of an embodiment used to sample material in waste drums. For brevity and clarity, a description of those parts which are identical or similar to those described in connection with the embodiment illustrated in FIGS. 1 and 2 will not be repeated here. Reference should be made to the foregoing paragraphs with the following description to arrive at a complete understanding of this second embodiment.

A waste profiling unit 400 allows for horizontal sampling and characterization operations of the grouted radwaste drums. The waste profiling unit 400 may be a floor mounted stainless steel containment unit comprising a plurality of chambers. For instance, the profiling unit 400 may contain a waste chamber 402 and a sampling chamber 404. The waste chamber may be sized such that it encloses a drum 406 of waste, such as radwaste. The waste chamber 402 may have a drum platform 408 for raising and rotating the drum 406 into position.

The sampling chamber 404 may also comprise access ports, posting out ports, viewing window, analysis area, sampling and sampling mechanism assembly area and wall fixtures with supporting legs with wheels (not shown). In some embodiments, the sample chamber has glove ports 410a–410d for hand access. The profiling unit 400 may also have viewing ports (not shown).

An automated sampling stage 412 contained within the sampling chamber 404 may orientate a drill bit 414 in and out of the drum 406. In one embodiment, the are four settings: (1) movement forward to bring the sampling mechanism to the mounted rubber seal access point on the side of the waste drum (this maintains containment as the sampling head is rotating and moving in and out of the drum); (2) movement of the sampling stage is a short sharp forward movement to pierce the metal of the drum; (3) a slow continuous pressure on the drilling end as the drilling end penetrates the grouted waste to allow optimum sample retrieval; (4) movement is a rapid removal from the drum to allow swapping of the sampling mechanism to prevent cross contamination of samples.

As in previous embodiments, the profiling containment unit 400 may have three major components: (1) a drill 416 with a specialized cutting and sampling bit 414, a sample collection unit 418 and a vacuum pump (not shown). The profiling containment unit 400 may be used in conjunction with in situ radiometric instruments to produce a profile of radiological or chemical contamination through the grouted material being studied. The drill bit 414 may be used under hammer action to penetrate the grouted waste. This causes the grouted material to be pulverized as the drill travels through the waste to efficiently transmitting to the sampling unit a representative sample of grouted material. The profiling equipment is designed to sequentially collect all material from the hole produced. As previously discussed, the waste samples may be continuously retrieved by use of a specially designed vacuumed sample retrieval unit that prevents cross contamination of the clean retrieved samples. No circulation medium is required with this profiling process; therefore, the only by-product from drilling is the sample.

The sample collection unit 418 may comprise a series of 350 cm$^3$, 4 um filter units 420a and 420b, housed in an aluminum casing 422. The units 420a and 420b are mounted in series inside the containment box to collect the powdered sample and to insure containment of dusts and volatile organics before the air passes to the vacuum pump. Sampled particulate travels from the specialized drill bit 414 to the first inline filter unit 420a where it may be collected and prevented from traveling to the secondary filter unit 420b, which acts as a secondary barrier to the vacuum pump. The filter units may be screwed into the aluminum housing 422 and sealed tight with a rubber o-ring (not shown) to maintain containment of the dusts and the integrity of the high vacuum. The removal of the filter units and its replacement are achieved by a simple screwing of the filter housing onto a manifold (not shown) of the sample collection unit. Powders are retrieved for radioanalysis by dispensing the powdered sample into a sealed containment vessel before being weighed out for appropriate radiometric measurement. Air passing through the primary and secondary inline filters then passes through a volatiles extraction unit 424 to trap volatiles released during sampling. The outlet of the vacuum pump may have a filter unit built into the pump mechanism to prevent any extraneous dusts being released to the working environment.

In one embodiment, the waste profiling unit 400 may be operated at flow rate of 55 CFM and at 27 inches Hg to retrieve the dusts and gasses generated into the inline sampling units. The entire waste profiling unit 400 may be operated under negative vacuum to ensure containment of radioactive dusts and gasses for safe sampling operations. Dimensions for such a unit may be 60×30×40 inches.

Figure 5:
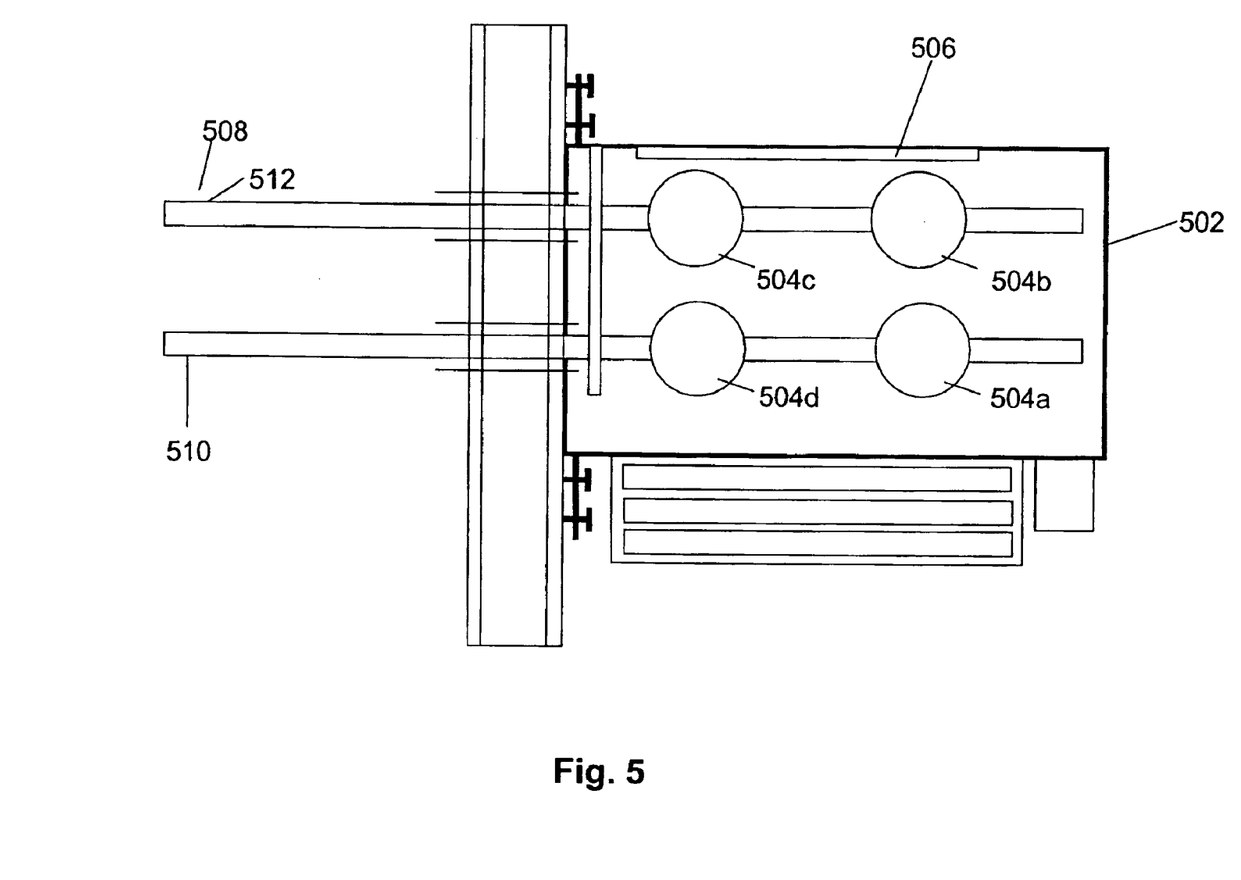
FIG. 5 is a schematic illustration of an alternative system.

Another embodiment is illustrated in FIG. 5, which is a system 500 used in conjunction with the containment technology for sealed room characterization of highly contaminated rooms. This embodiment samples sealed highly contaminated rooms and void spaces at sites as a means of preserving containment whilst sampling and characterizing the sealed room or void space, reducing time and costs as well as sample quality and turnaround time. Such an embodiment could be used for sampling and characterization of highly active inaccessible areas of a nuclear facility. The system 500 may sample materials in a sealed room 501 through a concrete wall 503.

The system 500 comprises a containment unit 502, which may be a wall or floor mounted stainless steel unit. The illustrative embodiments has a wall mounting 504a and 504b. The illustrative embodiment has glove ports 507a-507d for hand access and a viewing port 506. In the illustrative embodiment, the containment unit 502 is a horizontal box comprising access ports, posting out ports, viewing window, analysis area, sampling and video mechanism assembly area and wall fixtures with supporting legs with wheels. The dimensions for such a box may be 60×30×40 inches.

The containment unit 502 may comprise a video camera 508 which may be used to visually inspect the areas to be sampled and characterized and to identify any anomalies. The video camera 508 may also be used to observe sampling operations and positioning of drill bit 510. The video camera may have a illuminating light 515 to light up inaccessible areas of rooms.

As previously described, a sampling unit 509 may have three primary: a drill (not shown) with specialized cutting and sampling drill bits, a sample collection unit (not shown) and a vacuum pump (not shown). The equipment in conjunction with insitu radiometric instruments (not shown) may produce a profile of radiological or chemical contamination through the material being studied. The drill head may be used under hammer action to penetrate hard surfaces. This causes the bulk material to be pulverized as the drill travels through the radioactive media efficiently transmitting to the sampling unit a representative sample of bulk material as described above in reference to other embodiments.

The inline sampling unit (not shown) may be similar to the sampling unit described with reference to FIG. 4, in that it may comprise two, 350 cm$^3$, 4 um filter units, housed in an aluminum casing. The units may be mounted in series to collect the powdered sample and to insure containment of dusts before the air passes to the vacuum pump. Sampled particulate travels from the specialized drill bit to the first inline filter where they are collected and prevented from traveling to the secondary filter unit, which acts as a secondary barrier to the vacuum pump. The filter units may be screwed into the aluminum housing and sealed tight with a rubber o-ring to maintain containment of the dusts and integrity of the high vacuum. The removal of the filter unit and its replacement are achieved by a simple screwing of the filter housing onto the manifold of the filter-mounting unit. Powders are retrieved for radioanalysis by dispensing the powdered sample into a sealed containment vessel before being weighed out for appropriate radiometric measurement. The outlet of the vacuum pump may have a filter unit built into the pump mechanism to prevent any extraneous dusts being released to the working environment. The sampling unit may be operated at flow rate of 55 CFM and at 27 inches Hg to retrieval of dusts generated into the inline sampling unit. The containment unit 502 may be operated under negative vacuum to ensure containment of radioactive dusts for safe operator and all connections.

The entry ports 512a and 512b into the room or void space are constructed in a manner that provides sound anchorage of the containment technology unit, and are designed to easy transfer from one sampling point to the next. Each port may have a stainless steel box mounting plate with port cover that can be bolted tightly into place before and after sampling operations to maintain containment of contamination within the sealed room. The dimensions for these ports may be an internal diameter of 9 inches.

Sampling arms 514 may be assembled within the containment technology box and the video camera extended out through each of the entry ports 512a and 512b, respectively. These sampling arms may allow for the retrieval of surface samples from walls and floors. The distance into the room may be noted as sequential scans of the floor and wall area are carried out. A halogen light may be mounted behind the camera to illuminate surfaces for detailed viewing. Any physical anomalies such as debris, redundant equipment, evidence of the extent of spills and leaks, cracks and the physical condition of the surfaces are recorded for future viewing and referred to for sampling action strategies. Once initial viewing has been carried out the video equipment containment box may be moved to an adjacent port to be able to view sample acquisition by the sampling head mechanism and the profile drilling equipment.

The system 500 may include portable analysis equipment specifically designed to measure and calculate contamination levels of samples from within the containment unit 502.

In operation to collect surface samples, the sampling arms 514 may be assembled within the containment technology box via extension arms 518 and the sampling head mechanism extended out through each of the entry port 514a. The distance "d" into the room will be noted as sequential samples from the floor and opposite wall area are acquired for mapping of the radiochemical fingerprint from the surface throughout the contaminated room. Once the sampling head 510 is brought into position the sampling arm 514 may be rotated to release the sampling head and is then carefully lowered smoothly into close proximity to the surface to be sampled. This operation may be viewed by the video camera 513. The sampling head connecting wire (not shown) may then pulled a predetermined distance along the center of the sampling arm 514 and released to allow the sticky pad (not shown) on the sampling head mechanism to strike a floor. Pulling the connecting wire back along the length of the sampling arm retrieves the sample and sampling mechanism. With the sample positioned at the end of the sampling arm, it may be secured by rotating the sampling arm 514 180 degrees before retracting the arm back into the containment box 502. Before the sample is taken from the sampling head 510, it may be monitored for activity and placed into a plastic container (not shown) before transfer to the counting section of the containment technology box. The radiochemical activity levels may be obtained by a semi-quantitative counting method. This initial screening of the acquired samples allows more control and selection of samples sent for quantitative lab analysis via a sample collection box 520. Thus, elected samples may be transferred out of the containment unit 502 while maintaining containment.

The system 500 may also be used to obtain depth profiling of an opposite wall. Incremental samples to predetermined depths may be acquired and retrieved by the vacuum inline filter mechanism in the containment box as described in previous embodiments. Clean drill mechanisms and filters may be used at each sampling point to minimize cross contamination. A fiber optic cable may be positioned at the drill bit to allow for repositioning of the fresh drill bit into the initial hole to continue drilling into the cleaner bulk building material. Each of the incremental depth dust samples may be retrieved under vacuum along the length of the drill and sampling arm to be collected on a filter and then weighed and counted semi-quantitatively for contaminants, such as plutonium and americium activities. Selected samples of interest may be then sent to the lab for quantitative analysis.

While the invention has been described in reference to illustrative embodiments, the description is not to be construed in a limiting sense. Various modifications and combinations of the illustrative embodiments, as well as other embodiments of the invention, will be apparent to persons skilled in the art upon reference to the description.

What is claimed is:

1. A method of analyzing the amount of contaminants in building material, the method comprising:
   drilling into contaminated material an incremental distance to create a powder from the contaminated material,
   collecting the powder during the drilling by using a continuous vacuum force wherein the collecting comprises creating an air flow to move the powder through a flow passage within a drill bit such that the powder contacts a first filtration device in hermetic communication with the flow passage, analyzing the collected powder to determine the amount of contaminants in the contaminated material at the incremental distance, and providing a second filtration device in hermetic communication with the flow passage.

2. A method of analyzing the amount of contaminants in building material, the method comprising:

drilling into contaminated material an incremental distance to create a powder from the contaminated material, collecting the powder during the drilling by using a continuous vacuum force, analyzing the collected powder to determine the amount of contaminants in the contaminated material at the incremental distance, repeating the drilling, the collecting, and the analyzing at another location in the building material, and creating an activity profile of the contamination of the building material.

3. The method of claim 2 wherein the collecting comprises creating an air flow to move the powder through a flow passage within a drill bit such that the powder contacts a first filtration device in hermetic communication with the flow passage.

4. The method of claim 2 further comprising extracting the volatile compounds from induced air flow.

5. The method of claim 2 wherein the analyzing further comprises determining amounts of tritium contamination within the collected powder.

6. The method of claim 2 wherein the analyzing further comprises determining the level of radioactivity within the collected powder.

7. The method of claim 2 wherein the analyzing further comprises determining levels of chemical contamination within the collected powder.

8. A system for analyzing the amount of contaminants in building material, the system comprising:

a means for drilling into contaminated material an incremental distance to create a powder from the contaminated material, a means for collecting the powder during the drilling by using a continuous vacuum force wherein the collecting means composes a means for creating an air flow to move the powder through a flow passage within a drill bit such that the powder contacts a first filtration device in hermetic communication with the flow passage, a means for analyzing the collected powder to determine the amount of contaminants in the contaminated material at the incremental distance, and a means for providing a second filtration device in hermetic communication with the flow passage.

9. A system for analyzing the amount of contaminants in building material, the system comprising:

a means for drilling into contaminated material an incremental distance to create a powder from the contaminated material, a means for collecting the powder during the drilling by using a continuous vacuum force, a means for analyzing the collected powder to determine the amount of contaminants in the contaminated material at the incremental distance, and a means for creating an activity profile of the contamination of the building material.

10. The system of claim 9 further comprising a means for determining the incremental distance.

11. The system of claim 9 wherein the collecting means comprises a means for creating an air flow to move the powder through a flow passage within a drill bit such that the powder contacts a first filtration device in hermetic communication with the flow passage.

12. The system of claim 9 further comprising a means for extracting volatile compounds from induced air flow.

13. The system of claim 9 wherein the means for analyzing further comprises a means for determining amounts of tritium contamination within the collected powder.

14. The system of claim 9 wherein the means for analyzing further comprises a means for determining the level of radioactivity within the collected powder.

15. The system of claim 9 wherein the means for analyzing further comprises a means for determining levels of chemical contamination within the collected powder.

* * * * *

UNITED STATES PATENT AND TRADEMARK OFFICE
CERTIFICATE OF CORRECTION

PATENT NO. : 6,966,236 B2
DATED : November 22, 2005
INVENTOR(S) : Charters et al.

It is certified that error appears in the above-identified patent and that said Letters Patent is hereby corrected as shown below:

Column 4,
Line 49, change "sample" to -- samples --.

Column 9,
Line 31, delete "the".

Column 10,
Line 3, change "composes" to -- comprises --.

Signed and Sealed this

Fourth Day of April, 2006

JON W. DUDAS
*Director of the United States Patent and Trademark Office*